(12) United States Patent
Fleenor et al.

(10) Patent No.: US 7,351,407 B2
(45) Date of Patent: Apr. 1, 2008

(54) AGENTS WHICH REGULATE, INHIBIT, OR MODULATE THE ACTIVITY AND/OR EXPRESSION OF CONNECTIVE TISSUE GROWTH FACTOR (CTGF) AS A UNIQUE MEANS TO BOTH LOWER INTRAOCULAR PRESSURE AND TREAT GLAUCOMATOUS RETINOPATHIES/OPTIC NEUROPATHIES

(75) Inventors: Debra L. Fleenor, Crowley, TX (US); Allan Shepard, Fort Worth, TX (US); Nasreen Jacobson, Fort Worth, TX (US); Iok-Hou Pang, Grand Prairie, TX (US); Abbot F. Clark, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 282 days.

(21) Appl. No.: 10/510,585

(22) PCT Filed: Apr. 18, 2003

(86) PCT No.: PCT/US03/12521

§ 371 (c)(1),
(2), (4) Date: Oct. 8, 2004

(87) PCT Pub. No.: WO03/092584

PCT Pub. Date: Nov. 13, 2003

(65) Prior Publication Data

US 2005/0234075 A1    Oct. 20, 2005

Related U.S. Application Data

(60) Provisional application No. 60/376,606, filed on Apr. 30, 2002.

(51) Int. Cl.
*A61K 31/74* (2006.01)
(52) U.S. Cl. .................. 424/78.04; 424/400; 424/427
(58) Field of Classification Search .............. 424/400, 424/427, 78.04; 514/414, 424
See application file for complete search history.

(56) References Cited

U.S. PATENT DOCUMENTS

| | | | |
|---|---|---|---|
| 5,408,040 A | 4/1995 | Grotendorst et al. | |
| 5,585,270 A * | 12/1996 | Grotendorst et al. ..... | 435/252.3 |
| 5,594,015 A * | 1/1997 | Kurtz et al. ............... | 514/369 |
| 6,069,006 A | 5/2000 | Grotendorst et al. | |
| 6,150,101 A | 11/2000 | Grotendorst et al. | |
| 6,190,884 B1 | 2/2001 | Grotendorst et al. | |
| 6,232,064 B1 | 5/2001 | Grotendorst et al. | |
| 6,316,465 B1 * | 11/2001 | Pershadsingh et al. ...... | 514/310 |
| 6,348,329 B1 | 2/2002 | Schmidt et al. | |
| 6,358,741 B1 | 3/2002 | Schmidt et al. | |
| 2004/0005319 A1 | 1/2004 | Grotendorst et al. | |

FOREIGN PATENT DOCUMENTS

| | | | |
|---|---|---|---|
| AU | 2002 36641 A1 | 6/2003 | |
| WO | WO 00/30628 A2 | 6/2000 | |
| WO | WO 01/25226 A1 | 4/2001 | |
| WO | WO 01/60374 A1 | 8/2001 | |
| WO | WO 01/70727 A1 | 9/2001 | |
| WO | WO 02/13812 A1 | 2/2002 | |
| WO | WO 03/027275 A1 | 4/2003 | |
| WO | WO 03/049773 A | 6/2003 | |
| WO | WO 03/049773 A1 | 6/2003 | |
| WO | WO 03/092584 A2 | 11/2003 | |

OTHER PUBLICATIONS

Bain, J., H. McLauchlan, et al., "The Specificities of protein kinase inhibitors: an update" BIOCHEM J 371(Pt 1): 199-204 (2003).
Coghlan, M. P. et al., "Selective small molecule inhibitors of glycogen synthase kinase-3 modulate glycogen metabolism and gene transcription" CHEM BIOL 7(10):793-803 (2000).
Cohen, P. and Frame, S., "The renaissance of GSK3" Nat Rev Mol Cell Biol 2(10):769-776 (2001).
Davis, S. T. et al., "Prevention of chemotherapy-induced alopecia in rats by CDK inhibitors" SCIENCE 291(5501):134-137 (2001).
Hardcastle, I. R. et al., "Designing inhibitors of cyclin-dependent kinases" Annu Rev Pharmacol Toxicol 42:325-348 (2002).
Knockaert, M. et al., "Pharmacological inhibitors of cyclin-dependent kinases" Trends Pharmacol Sci 23(9):417-425 (2002).
Kothapalli, D. and Grotendorst, G.R., "CTGF modulates cell cycle progression in cAMP-arrested NRK fibroblasts" J Cell Physiol 182(1):119-126 (2000).
Leost, M. et al., "Paullones are potent inhibitors of glycogen synthase kinase-3beta and cyclin-dependent kinase 5/p25" Eur J Biochem 267(19):5983-5994 (2000).
Leske MC, et al., American Journal of Epidemiology, 118(2):166-191 (Aug. 1983).
Park, S. K., Kim, J., Seomun, Y., Choi, J., Kim, D. H., Han, I. O., Lee, E. H., Chung, S. K., Joo, C. K., "Hydrogen Peroxide is a Novel Inducer of Connective Tissue Growth Factor," Biochem. Biophys. Res. Commun. 284(4):966-971 (2001).
Schwab, J. M., Postler, E., Nguyen, T. D., Mittelbronn, M., Meyermann, R., Schluesener, H. J., "Connective Tissue Growth Factor is Expressed by a Subset of Reactive Astrocytes in Human Cerebral Infarction," Neuropathology and Appied. Neurobiology 26(5):434-440 (2000).
Schwab, J. M., Beschorner, R., Nguyen, T. D., Meyermann, R., Schluesener, H. J., Differential Cellular Accumulation of Connective Tissue Growth Factor Defines a Subset of Reactive Astrocytes, Invading Fibroblasts, and Endothelial Cells Following Central Nervous System Injury in.
Shepard et al., "Delayed Secondary Glucocorticoid Responsiveness of MYOC in Human Trabecular Meshwork Cells", IOVS 42:3173-3181 (2001).

(Continued)

*Primary Examiner*—Ruth A Davis
(74) *Attorney, Agent, or Firm*—Mark E. Flanigan (57) ABSTRACT

The present invention provides a method for lowering intraocular pressure and providing neuroprotection to a patient in need thereof by administering a therapeutically effective amount of at least one non-nucleotide or non-protein agent that inhibits expression and/or signaling of connective tissue growth factor (CTGF).

11 Claims, 3 Drawing Sheets

OTHER PUBLICATIONS

Strong, N. P., "How optometrists screen for glaucoma: A survey", Ophthal. Physiol. Opt., 12:3-7 (1992).

Vaughan, D. et al., In: General Ophthalmology, Appleton & Lange, Norwalk, Conn., pp. 213-230 (1992).

Wang et al., "Optimal procedure for extracting RNA from human ocular tissues and expression profiling of the congential glaucoma gene FOXC1 using quantitativ RT-PCR", Mol. Vis. 7:89-94 (2001).

Willson, T. M. et al., "The PPARs: from orphan receptors to drug discovery" J Med Chem 43(4):527-550 (2000).

Woodgett, J. R., "Judging a protein by more than its name: GSK-3" Science's STKE 2001(100):1-11 (2001).

Zaharevitz, D. W. et al., "Discovery and initial characterization of the paullones, a novel class of small-molecule inhibitors of cyclin-dependent kinases" Cancer Res 59(11):2566-2569 (1999).

Francesca et al., "Human Anti-Transforming Growth Factor-•2 Antibody: A New Glaucoma Anti-Scarring Agent", IOVS, vol. 40:2225-2234, 1999.

Lefevre et al., "Involvement of Cyclin-Dependent Kinases in Axotomy Induced Retinal Ganglion Cell Death", The Journal of Comparative Neurology, vol. 447:72-81, 2002.

Mass et al., "Apoptosis of Central and Peripheral Neurons Can Be Prevented with Cyclin-Dependent Kinase/Mitogen-Activated Protein Kinase Inhibitors", Journal of NeuroChemistry, vol. 70:1401-1410, 1998.

Partial European Search Report dated Dec. 21, 2005 for corresponding EP Patent Application No. 05109789.7.

* cited by examiner

AGENTS WHICH REGULATE, INHIBIT, OR MODULATE THE ACTIVITY AND/OR EXPRESSION OF CONNECTIVE TISSUE GROWTH FACTOR (CTGF) AS A UNIQUE MEANS TO BOTH LOWER INTRAOCULAR PRESSURE AND TREAT GLAUCOMATOUS RETINOPATHIES/OPTIC NEUROPATHIES

This application claims priority from PCT/US03/12521 filed on Apr. 18, 2003, and U.S. Ser. No. 60/376,606, filed on Apr. 30, 2002.

BACKGROUND OF THE INTENTION

1. Field of the Invention

The present invention relates to the field of ocular conditions involving neurodegeneration and/or elevated intraocular pressure. More specifically, the invention provides compositions that lower intraocular pressure and provide ocular neuroprotection.

2. Description of the Related Art

There are a number of ocular conditions that are caused by, or aggravated by, damage to the optic nerve head, degeneration of ocular tissues, and/or elevated intraocular pressure. For example, "glaucomas" are a group of debilitating eye diseases that are a leading cause of irreversible blindness in the United States and other developed nations. Primary Open Angle Glaucoma ("POAG") is the most common form of glaucoma. The disease is characterized by the degeneration of the trabecular meshwork, leading to obstruction of the normal ability of aqueous humor to leave the eye without closure of the space (e.g., the "angle") between the iris and cornea (Vaughan, D. et al., (1992)). A characteristic of such obstruction in this disease is an increased intraocular pressure ("IOP"), resulting in progressive visual loss and blindness if not treated appropriately and in a timely fashion. The disease is estimated to affect between 0.4% and 3.3% of all adults over 40 years old (Leske, M. C. et al. (1986); Bengtsson, B. (1989); Strong, N. P. (1992)). Moreover, the prevalence of the disease rises with age to over 6% of those 75 years or older (Strong, N. P., (1992)).

Glaucoma affects three separate tissues in the eye. The elevated IOP associated with POAG is due to morphological and biochemical changes in the trabecular meshwork (TM), a tissue located at the angle between the cornea and iris. Most of the nutritive aqueous humor exits the anterior segment of the eye through the TM. The progressive loss of TM cells and the build-up of extracellular debris in the TM of glaucomatous eyes leads to increased resistance to aqueous outflow, thereby raising IOP. Elevated IOP, as well as other factors such as ischemia, cause degenerative changes in the optic nerve head (ONH) leading to progressive "cupping" of the ONH and loss of retinal ganglion cells and axons. The detailed molecular mechanisms responsible for glaucomatous damage to the TM, ONH, and the retinal ganglion cells are unknown.

Twenty years ago, the interplay of ocular hypertension, ischemia and mechanical distortion of the optic nerve head were heavily debated as the major factors causing progression of visual field loss in glaucoma. Since then, other factors including excitotoxicity, nitric oxide, absence of vital neurotrophic factors, abnormal glial/neuronal interplay and genomics have been implicated in the degenerative disease process. The consideration of genomics deserves some discussion insofar as it may ultimately define the mechanism of cell death, and provide for discrimination of the various forms of glaucoma. Within the past 8 years, over 15 different glaucoma genes have been mapped and 7 glaucoma genes identified. This includes six mapped genes (GLC1A-GLC1F) and two identified genes (MYOC and OPTN) for primary open angle glaucoma, two mapped genes (GLC3A-GLC3B) and one identified gene for congentical glaucoma (CYP1B1), two mapped genes for pigmentary dispersion/pigmentary glaucoma, and a number of genes for developmental or syndromic forms of glaucoma (FOXC1, PITX2, LMX1B, PAX6).

Thus, each form of glaucoma may have a unique pathology and accordingly a different therapeutic approach to the management of the disease may be required. For example, a drug that effects the expression of enzymes that degrade the extracellular matrix of the optic nerve head would not likely prevent RGC death caused by excitotoxicity or neurotrophic factor deficit. In glaucoma, RGC death occurs by a process called apoptosis (programmed cell death). It has been speculated that different types of insults that can cause death may do so by converging on a few common pathways. Targeting downstream at a common pathway is a strategy that may broaden the utility of a drug and increase the probability that it may have utility in the management of different forms of the disease. However, drugs that effect multiple metabolic pathways are more likely to produce undesirable side-effects. With the advent of gene-based diagnostic kits to identify specific forms of glaucoma, selective neuroprotective agents can be tested with the aim of reducing is the degree of variation about the measured response.

Current glaucoma therapy is directed to lowering IOP, a major risk factor for the development and progression of glaucoma. These therapies lower IOP, but they do not directly address the pathogenic mechanisms, and the disease continues to progress. Thus, what is needed is a therapeutic method for lowering IOP and/or providing neuroprotection to the optic nerve head and/or to retinal ganglion cells via pathogenic pathways.

SUMMARY OF THE INVENTION

The present invention overcomes these and other drawbacks of the prior art by providing a method for lowering intraocular pressure and providing neuroprotection to a patient in need thereof by administering a therapeutically effective amount of a composition including at least one non-nucleotide or non-protein agent that inhibits expression and/or signaling of connective tissue growth factor (CTGF), and a pharmaceutically acceptable carrier. In another aspect, the invention provides a method for lowering intraocular pressure by administering to a patient a therapeutically effective amount of an agent that inhibits expression and/or signaling of CTGF. Preferably, the compositions for use in the method of the invention will lower intraocular pressure that is elevated due to an increased expression of CTGF or of a product of CTGF signaling.

In preferred embodiments, the composition of the invention may be administered by topical application, intracamerally or via an implant. Typically, the total concentration of the CTGF inhibitor in the composition of the invention will be from 0.01% to 2%. Generally, the treatment method of the invention will be most useful for a patient suffering from glaucoma, for example normal-tension glaucoma, or ocular hypertension.

The invention further provides a method for preventing the visual field loss associated with POAG by administering to a patient in need thereof a composition including a non-nucleotide or non-protein agent that modulates the expression and/or signaling of CTGF such that intraocular pressure is controlled and protection is provided to retinal ganglion cells or to the optic nerve head.

In another embodiment, the present invention provides a composition for lowering intraocular pressure and providing neuroprotection in a patient in need thereof. Generally, the composition of the invention includes at least one agent that inhibits the expression and/or signaling of connective tissue growth factor (CTGF) and a pharmaceutically acceptable carrier. The total concentration of CTGF in the composition of the invention will preferably be from 0.01% to 2%.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. CTGF gene expression is elevated in glaucomatous vs. normal TM tissues. To verify the results of the microarray and cDNA subtraction, CTGF mRNA expression was determined by QPCR analysis of normal vs. glaucoma TM tissue cDNA. The numbers below each sample refer to the cDNA identification number assigned to each sample. Human donor tissue and total RNA were obtained as described (Wang et al. 2001). "Ave." represents the mean of normal or glaucoma TM levels.

DETAILED DESCRIPTION PREFERRED EMBODIMENTS

Glaucoma is a heterogeneous group of optic neuropathies that share certain clinical features. The loss of vision in glaucoma is due to the selective death of retinal ganglion cells in the neural retina that is clinically diagnosed by characteristic changes in the visual field, nerve fiber layer defects, and a progressive cupping of the ONH. One of the main risk factors for the development of glaucoma is the presence of ocular hypertension (elevated, intraocular pressure, IOP). IOP also appears to be involved in the pathogenesis of normal tension glaucoma where patients have what is often considered to be normal IOP. The elevated IOP associated with glaucoma is due to elevated aqueous humor outflow resistance in the trabecular meshwork (TM), a small specialized tissue located in the iris-corneal angle of the ocular anterior chamber. Glaucomatous changes to the TM include a loss in TM cells and the deposition and accumulation of extracellular debris including plaque-like material. In addition, there also are changes that occur in the glaucomatous optic nerve head. In glaucomatous eyes, there are morphological and mobility changes in ONH glial cells. In response to elevated IOP and/or transient ischemic insults, there is a change in the composition of the ONH extracellular matrix and alterations in the glial cell and retinal ganglion cell axon morphologies.

Glaucomatous changes to the TM differ from fibrosis, which is associated with a wound healing response and generally involves inflammation and the subsequent proliferation of myofibroblasts. Tissue injury is recognized by the inflammatory system, which initiates a wound repair process by stimulating fibroblasts and angiogenesis. Dead or dying tissues/cells are replaced by scar tissue consisting initially of fibrin, which is subsequently replaced by excessive amounts of extracellular matrix material, particularly collagen.

CTGF is a secreted cytokine which is known to increase extracellular matrix (ECM) production, primarily via increased deposition of collagen I and of fibronectin. Overexpression of CTGF has previously been implicated as a major causative factor in conditions such as scleroderma, fibroproliferative diseases, scarring, etc. in which there is an overaccumulation of ECM components. An overaccumulation of extracellular matrix materials in the region of the trabecular meshwork (TM) is also a hallmark of many forms of glaucoma; such increases are believed to lead to increased resistance to aqueous outflow, and therefore elevated intraocular pressures. The present inventors have discovered the presence of CTGF gene products in isolated tissues and cell lines established from human TM. Thus, it is believed that CTGF plays a role in ECM production by the TM. Agents which down-regulate CTGF gene expression, protein production, or down-stream effects of CTGF activation, represent a novel means for lowering IOP.

CTGF expression can be induced by a wide variety of factors including: TGF-β, VEGF, thrombin, advanced glycation end-products (AGE), mechanical stress, and lysophosphatidic acid (LPA), among others. The specific inducers of CTGF and the signaling pathways can vary depending on the specific cell type being stimulated. There are reports of TGF-β induction of CTGF involving Smads, PLC, PKC, and tyrosine linases in some cell types while RhoA, PKA, and the cytoskeleton appear to be involved in other cell types. Mechanical stress of fibroblasts induces CTGF expression via involvement of protein kinases and tyrosine phosphatases.

The mechanism of action of CTGF is not well understood. CTGF appears to bind to PDGF receptors, integrins, and LDL receptor-related proteins (LRP), each of which may act as a signaling cell surface receptor for CTGF. In some cell types, CTGF signaling through PDGF receptors appears to involve MAPK and PI3K. CTGF signaling in chondrocytes involves ERK signaling for cell proliferation and p38MAPK signaling for cellular differentiation. The specific cell surface receptors and signaling pathways used by CTGF appear to be dependent on the specific cell type being studied.

U.S. Pat. No. 5,585,270 describes polynucleotides encoding CTGF. CTGF is said to have mitogenic activity, or the ability to stimulate target cells to proliferate. It is also said to have chemotactic activity, that is, the chemically induced movement of cells as a result of interaction with particular molecules. The protein is believed to play a role in the normal development, growth and repair of human tissue. The patent also describes a method for accelerating wound healing in a subject by applying to the wound an effective amount of a composition containing purified CTGF. The polypeptide is said to be useful in cases where there is impaired healing of skin wounds or there is a need to augment the normal healing mechanisms, e.g., burns. The patent contains no discussion of glaucoma or eye disorders.

U.S. Pat. No. 6,069,006, whose specification is a continuation-in-part of U.S. Pat. No. 5,585,270 discussed above, describes CTGF regulatory nucleic acid sequences. This patent further describes methods for treating fibrotic diseases and for identifying agents for treatment of fibrotic diseases. No specific agents, other than CTGF nucleic acid sequences or polypeptides are described. Neuroprotection of ocular tissues is not described.

U.S. Pat. No. 6,358,741 describes a number of nucleic acid sequences derived from CTGF that are said to be useful for inhibiting the expression of CTGF in a cell. This patent does not discuss glaucoma, neuroprotection of ocular tissues or non-nucleic acid or non-polypeptide sequences for inhibiting CTGF expression.

CTGF appears to accrue in high concentrations in the cytoplasm of stellate reactive astrocytes of the central nervous system. It has been implicated as a causative agent in mechanisms associated with reactive astrocytosis such as gliosis (glial overgrowth) and glial scar formation, i.e., in processes known to hinder neural repair and growth (Schwab et al. 2000; Schwab et al. 2001). It is believed that such processes also participate in the loss of retinal neurons and/or the inability to repair optic nerve axons associated with glaucoma. The present inventors have discovered that downregulation of CTGF provides a means for protection of both the retina and the optic nerve/nerve head.

Thus, in one aspect, the present invention provides a method for lowering IOP and providing neuroprotection to retinal ganglion cells by administering a composition including a non-nucleotide or non-peptidyl CTGF inhibitor. It is further contemplated that the composition could include a compound that inhibits an agent which upregulates CTGF. For example, hydrogen peroxide ($H_2O_2$) has been shown to be an inducer of CTGF gene expression. TGF-β, dexamethasone and serotonin have also been found to induce CTGF expression (Park et al. 2001).

The therapeutic agent for the treatment of glaucoma will preferably be a small drug-like molecule, which affects one or more aspects of the CTGF pathway. Preferred therapeutic agents are those that are: (1) inhibitors of CTGF; (2) inhibitors of agents acting downstream of CTGF action (i.e., inhibitors of CTGF signaling) and/or (3) inhibitors of agents that upregulate CTGF gene or protein expression.

The inventors have tested several different compound classes in a CTGF QPCR assay for inhibition of basal and TGFβ2-induced CTGF gene expression in cultured human normal or glaucomatous TM cells. Small molecule inhibitors were targeted at the inhibition of GSK-3, CDK, NAALADase, Protein Kinase C, MEK, p38MAPK, ROCK, VEGF, geranylgeranyl transferase and AGE. Small molecule agonists of PPAR, 5-HT, and P2X7 were also tested for activity. Compounds which target extracellular signal-regulated kinase 1 or 2 (ERK1 or ERK2) may also play a role in basal or TGFβ2-induced CTGF gene expression. There is significant cross-reactivity of many of the GSK-3 and CDK inhibitors and it is possible that compounds that inhibit other targets such as the ERK's, Protein Kinase C, or STAT families may prove valuable in the inhibition of basal or TGFβ2-stimulated CTGF in TM cells.

Two general compound classes have been found to inhibit both basal and TGFβ2-induced CTGF expression in human TM cells: GSK-3 and CDK inhibitors. Glycogen synthase kinase (GSK-3) is a serine/threonine protein kinase that is present as two cellular forms, GSK-3α and GSK-3β, derived from two genes. GSK-3α and GSK-3β are 95% identical and their differential inhibition by small molecule antagonists cannot be readily distinguished. GSK-3 is the rate limiting enzyme in glycogen synthesis but has many cellular targets of phosphorylation including glycogen synthase, β-catenin, eIF2B, and tau (reviewed in (Cohen and Frame 2001) and (Woodgett 2001)). The direct involvement of GSK-3 in CTGF expression and signaling is unexampled in the literature.

Cyclin-dependent kinases (CDKs) have multiple cellular functions including the regulation of cell division cycle, apoptosis, transcription, neuronal function, and differentiation. Several known ATP-competitive inhibitors of CDK have been identified (Knockaert, Greengard et al. 2002). CDK inhibition is being pursued for use in the treatment of cancer, Alzheimer's, ALS, stroke, cardiovascular disease and others. CTGF has been shown to be a downstream mediator of TGFβ in fibroblast proliferation by upregulation of cyclin A-cdk2 (Kothapalli and Grotendorst 2000).

Figure 1:
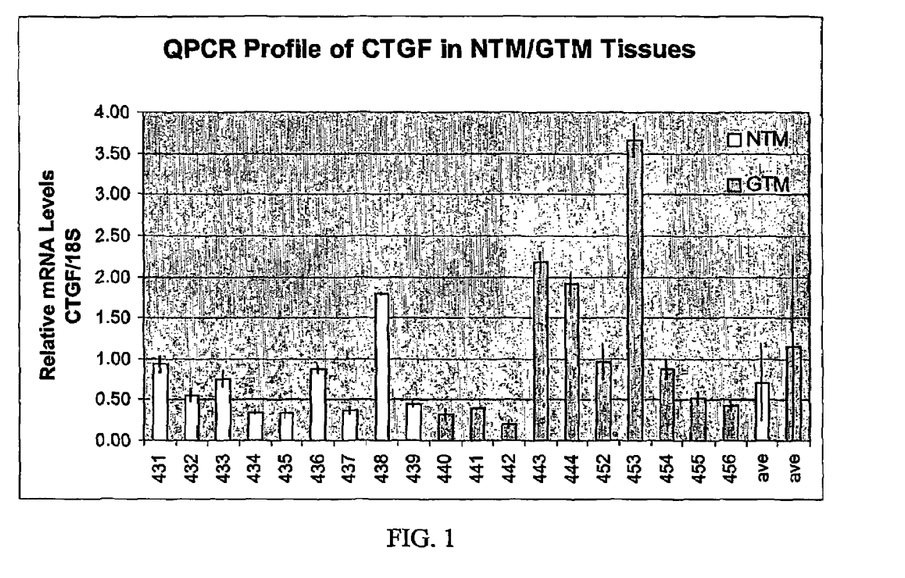
Figure 2:
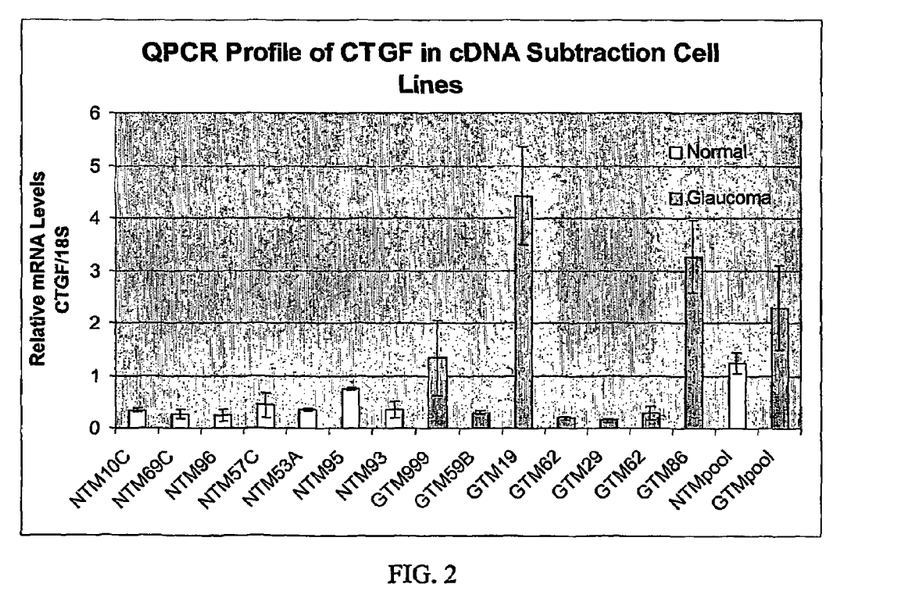
FIG. 2. CTGF gene expression is elevated in glaucomatous vs. normal TM cell lines. To verify the results of the microarray and cDNA subtraction, CTGF mRNA expression was determined by QPCR analysis of normal vs. glaucoma TM cell line cDNA. The numbers below each sample refer to the cell line identification number. Human TM cell lines and total RNA were obtained as described (Shepard et al. 2001). "NTM pool" and "GTM pool" refer to amplification levels from pooled NTM or GTM cDNA.
Figure 3:
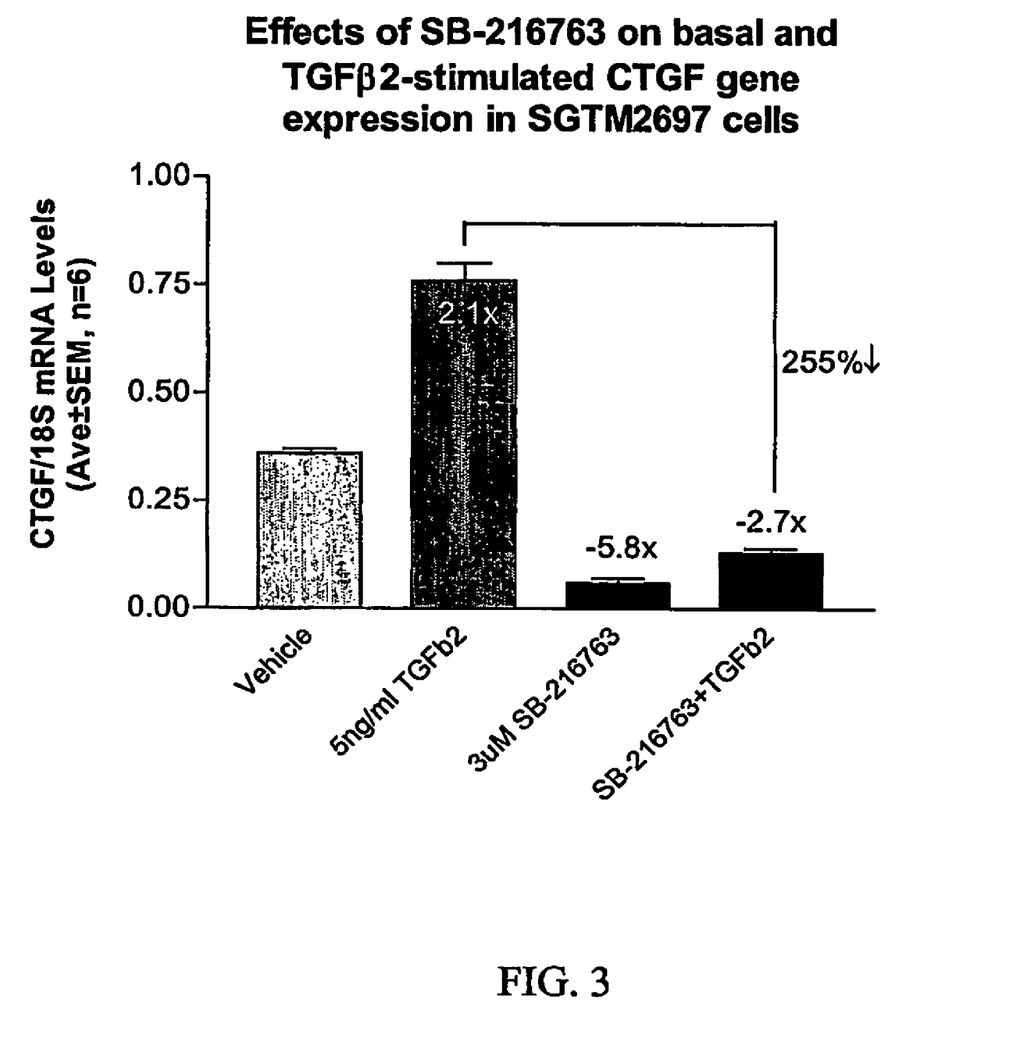
FIG. 3. Effect of GSK-3 inhibition on CTGF gene expression in glaucomatous TM cells. To determine the effects of GSK-3 inhibition on CTGF gene expression, we measured the effects of the known GSK-3 inhibitor SB-216763 (Coghlan, et al. 2000) on both basal and TGFβ2-stimulated CTGF mRNA expression in a glaucomatous TM cell line (SGTM2697) using QPCR analysis.

Within the GSK-3 class of compounds, one compound, SB-216763 (Coghlan, Culbert et al. 2000), was found to inhibit both basal and TGFβ2-induced CTGF levels in normal and glaucomatous (FIG. 3) human TM cells. SB-216763 is a maleimide derivative with an $IC_{50}$ of 34 nM against GSK-3α and GSK-3β in the presence of 0.01 mM ATP and a $K_i$ of 9 nM (Coghlan, Culbert et al. 2000). Other compounds in the GSK-3 class of inhibitors tested and found to inhibit basal and, in some cases, TGFβ2-induced CTGF gene expression in TM cells included the paullones such as alsterpaullone, 9-cyanopaullone and kenpaullone (Zaharevitz, Gussio et al. 1999; Leost, Schultz et al. 2000; Bain, McLauchlan et al. 2003).

Figure 4:
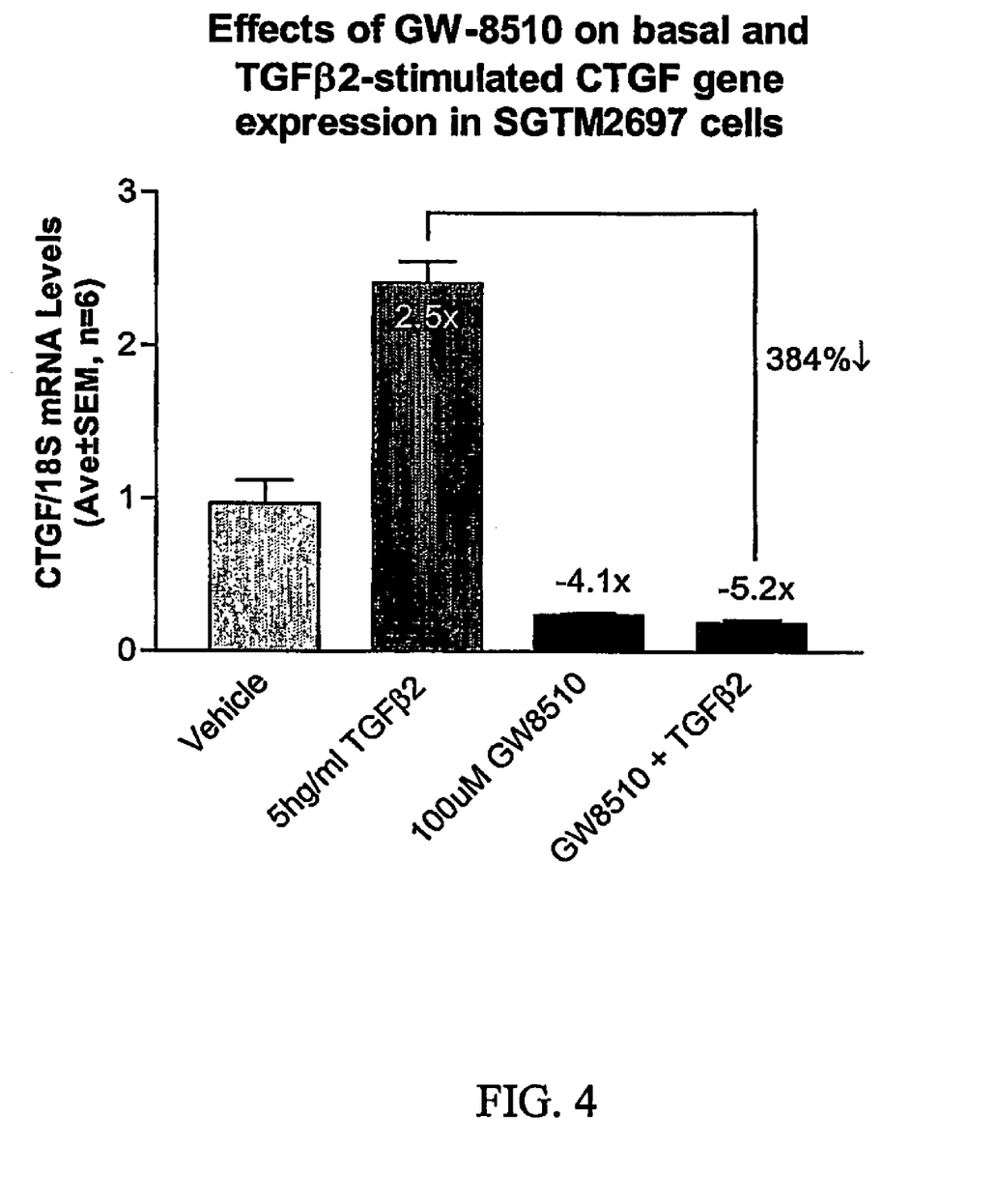
FIG. 4. Effect of CDK2 inhibition on CTGF gene expression in glaucomatous TM cells. To determine the effects of CDK inhibition on CTGF gene expression, we measured the effects of the known CDK2 inhibitor GW-8510 (Davis, et al. 2001) on both basal and TGFβ2-stimulated CTGF mRNA expression in a glaucomatous TM cell line (SGTM2697) using QPCR analysis.

Within the CDK class of compounds, a relatively selective CDK2 inhibitor, GW-8510 (Davis, Benson et al. 2001), was found to inhibit both basal and TGFβ2-induced CTGF levels in normal and glaucomatous (FIG. 4) human TM cells. GW-8510 is a potent and relatively select inhibitor of CDK2 with an $IC_{50}$ of 10 mM. GW-8510 also inhibits CDK1 and CDK4 but with lower $IC_{50}$ values (110 and 130 nM) (Davis, Benson et al. 2001). Other CDK class inhibitors tested and shown to have inhibitory activity included purvalanol A and roscovitine (Hardcastle, Golding et al. 2002).

Other classes of compounds tested in the CTGF QPCR assay and found to inhibit basal and, in some cases, TGFβ2-induced CTGF gene expression in TM cells included PPAR agonists such as troglitazone, ciglitazone (Willson, Brown et al. 2000) and 15(S)HETE.

The agents of this invention, can be incorporated into various types of ophthalmic formulations for delivery to the eye (e.g., topically, intracamerally, or via an implant). The agents are preferably incorporated into topical ophthalmic formulations for delivery to the eye. The agents may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving an agent in a physiologically acceptable isotonic aqueous buffer. Further, the ophthalmic solution may include an ophthalmologically acceptable surfactant to assist in dissolving the agent. Furthermore, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the agent in a hydrophilic base prepared from the combination of, for example, carbopol-974, or the like, according to the published formulations for analogous ophthalmic preparations; preservatives and tonicity agents can be incorporated.

The agents are preferably formulated as topical ophthalmic suspensions or solutions, with a pH of about 4 to 8. The establishment of a specific dosage regimen for each individual is left to the discretion of the clinicians. The agents will normally be contained in these formulations in an amount 0.01% to 5% by weight, but preferably in an amount of 0.05% to 2% and most preferably in an amount 0.1 to 1.0% by weight. The dosage form may be a solution, suspension microemulsion. Thus, for topical presentation 1 to 2 drops of these formulations would be delivered to the surface of the eye 1 to 4 times per day according to the discretion of a skilled clinician.

The agents can also be used in combination with other agents for treating glaucoma, such as, but not limited to, β-blockers, prostaglandin analogs, carbonic anhydrase inhibitors, $α_2$ agonists, miotics, and neuroprotectants.

The agent may be delivered directly to the eye (for example: topical ocular drops or ointments; slow release devices in the cul-de-sac or implanted adjacent to the sclera or within the eye; periocular, conjunctival, sub-Tenons, intracameral or intravitreal injections) or parenterally (for example: orally; intravenous, subcutaneous or intramuscular injections; dermal delivery; etc.) using techniques well known by those skilled in the art. The following are examples of possible formulations embodied by this invention.

| (a) Topical ocular formulation | wt. % |
|---|---|
| CTGF Inhibitor | 0.005-5.0 |
| Tyloxapol | 0.01-0.05 |
| HPMC | 0.5 |
| Benalkonium chloride | 0.01 |
| Sodium chloride | 0.8 |
| Edetate disodium | 0.01 |
| NaOH/HCl | q.s. pH 7.4 |
| Purified water | q.s. 100 mL |

It is further contemplated that the compounds of the invention could be formulated in intraocular insert devices.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Expression of CTGF in Glaucomatous TM vs Non-glaucomatous TM

Microarray Screen

The mRNA transcript for CTGF was identified as being elevated in glaucomatous TM cells vs. normal TM cells by a GeneFilter® (Research Genetics) screen.

Five hundred ηg of total RNA (TRIzol Reagent; Invitrogen) was isolated from pooled (6 each) normal or glaucomatous TM cell lines as described (Shepard et al., IOVS 2001, 42:3173) and reverse-transcribed separately in the presence of 300 units of Superscript II RNase H— reverse transcriptase (Invitrogen), 100 μCi [$α$-$^{33}$P]dCTP (10 mCi/ml, 3,000 Ci/mmol; Amersham), 0.33 mM dATP, dGTP, dCTP (Promega), 3.3 mM DTT, 1×First Strand Buffer (Invitrogen), and 2 μg oligo-dT at 37° C. for 90 min. The radiolabeled cDNA was subsequently purified with Chroma-Spin 100 Columns (Clontech) according to the manufacturer's instructions. A single Genefilter® (GF211; Research Genetics) spotted with ≈4,000 known genes was used for hybridization with radiolabeled probe according to the manufacturer's instructions. The membrane was first pretreated by boiling in 0.5% SDS for 5 min. Prehybridization of the membrane was performed for 30 min at 42° C. in roller bottles containing 5 ml MicroHyb (Research Genetics) with 5 ug poly-dA (Research Genetics) and 5 μg boiled Cot1 DNA (Invitrogen) as blocking reagents. The entire radiolabeled probe was boiled and added to the prehybridization mixture for 16 h at 42° C. Following hybridization, the membranes were washed twice in 2×SSC/1% SDS for 20 min and then once in 0.5×SSC/1% SDS for 15 min. The membrane was placed on wet Whatmann 3 MM paper and wrapped in Saran Wrap. Images were acquired on a Storm Phosphorimager (Molecular Dynamics) using maximum resolution. Once the image was acquired the blot was immediately stripped in boiling 0.5% SDS and subjected to another hybridization with the opposite probe, e.g. normal TM followed by glaucomatous TM. Images from duplicate probings were analyzed using Pathways (Research Genetics) and MS Excel (Microsoft) software. Of the 4300 genes on the GF211 GeneFilter®, CTGF (GenBank accession #AA598794) was one of 7 genes that showed a GTM:NTM ratio >2-fold.

cDNA Subtraction Screen

CTGF was identified independently in a custom PCR-Select™ cDNA Subtraction screen (Clontech) used to screen for mRNA transcripts that are differentially expressed in glaucomatous vs. normal TM cells.

Seven hundred μg of total RNA (TRIzol Reagent; Invitrogen) was isolated from pooled (7 each) normal or glaucomatous TM cell lines as described (Shepard et al. 2001). Tester (glaucomatous) and driver (normal) poly A+ RNA was isolated by two rounds of poly A+ selection on oligo-dT latex beads using a Nucleotrap mRNA Midi kit (Clontech). All subsequent PCR-Select™ cDNA Subtraction steps were performed according to Clontech kit (catalog # K1804-1) methodology.

Differential screening of the resulting cDNA subtraction libraries was performed essentially according to instructions in the PCR-Select™ Differential Screening Kit (Clontech catalog # K1808-1). A select number of differentially expressed cDNA clones were also confirmed by virtual Northern analysis. A list of all the candidate differentially expressed clones identified with subtracted TM cell cDNA library probe was generated by Clontech. The transcript for CTGF (GenBank accession # XM_037055.1) was in this list and was enriched in the glaucomatous cDNA library.

EXAMPLE 2

RNA Isolation and First Strand cDNA Preparation

Total RNA was isolated from TM cells using Trizol® reagent according to the manufacturer's instructions (Life Technologies). First strand cDNA was generated from 1 ug of total RNA using random hexamers and TaqMan® Reverse Transcription reagents according to the manufacturer's instructions (PE Biosystems, Foster City, Calif.). The 100 ul reaction was subsequently diluted 20-fold to achieve an effective cDNA concentration of 0.5 ng/ul.

Quantitative PCR

Differential expression of CTGF was verified by quantitative real-time RT-PCR (QPCR) using an ABI Prism® 7700 Sequence Detection System (Applied Biosystems). essentially as described (Shepard et al., IOVS 2001, 42:3173). Primers for CTGF amplification were designed using Primer Express software (Applied Biosystems) and anneal to adjacent exons of Genbank accession # NM_001901.1 (CAGCTCTGACATTCTGATTCGAA, nts 1667-1689 and TGCCACAAGCTGTCCAGTCT, nts 1723-1742) and generate a 76-bp amplicon. Amplification of CTGF was normalized to 18S ribosomal RNA expression using primers designed to the 18S rRNA gene (GenBank accession #X03205 GTCCCTGCCCTTTGTACACAC, nts 1680-1700 and CGATCCGAGGGCCTCACTA, nts 1730-1749) which generates a 69-bp amplicon. The SYBR® Green I double-stranded DNA binding dye chemistry (Applied Biosystems) was used to amplify CTGF or 18S cDNA. Specificity of the CTGF and 18S primer pairs was assessed from the PCR product by a combination of DNA sequencing, agarose gel analysis and dissociation curve analysis using the ABI Prism 770 SDS Dissociation Curve software (Applied Biosystems). CTGF or 18S rRNA reactions consisted of 1×SYBR Green PCR Master Mix (Applied Biosystems), 50 nM primer concentrations and 2.5 ng cDNA in a final volume of 50 ul. Thermal cycling conditions consisted of 50° C., 2 min, 95° C. 10 min followed by 40 cycles at 95° C., 15 sec, 60° C., 1 min. Quantification of relative RNA concentrations was done using the relative standard curve method as described in PE Biosystems User Bulletin #2 (http://docs.appliedbiosystems.com/pebiodocs/04303859.pdf). Data analysis was performed with SDS software version 1.9.1 (Applied Biosystems) and MS Excel 97 (Microsoft). Plasmid DNA containing target sequence for CTGF or 18S was used for generating the standard curve. QPCR data are presented as mean±SD.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. Nos. 6,069,006 6,358,741

Books

Other Publications

Bain, J., H. McLauchlan, et al., "*The specificities of protein kinase inhibitors: an update*" BIOCHEM J 371(Pt 1):199-204 (2003).

Coghlan, M. P. et al., "*Selective small molecule inhibitors of glycogen synthase kinase-3 modulate glycogen metabolism and gene transcription*" CHEM BIOL 7(10):793-803 (2000).

Cohen, P. and Frame, S., "*The renaissance of GSK3*" NAT REV MOL CELL BIOL 2(10):769-776 (2001).

Davis, S. T. et al., "*Prevention of chemotherapy-induced alopecia in rats by CDK inhibitors*" SCIENCE 291(5501):134-137 (2001).

Hardcastle, I. R. et al., "*Designing inhibitors of cyclin-dependent kinases*" ANNU REV PHARMACOL TOXICOL 42:325-348 (2002).

Knockaert, M. et al., "*Pharmacological inhibitors of cyclin-dependent kinases*" TRENDS PHARMACOL SCI 23(9):417-425 (2002).

Kothapalli, D. and Grotendorst, G. R., "*CTGF modulates cell cycle progression in cAMP-arrested NRK fibroblasts*" J CELL PHYSIOL 182(1):119-126 (2000).

Leost, M. et al., "*Paullones are potent inhibitors of glycogen synthase kinase-3beta and cyclin-dependent kinase 5/p25*" EUR J BIOCHEM 267(19):5983-5994 (2000).

Park, S. K., Kim, J., Seomun, Y., Choi, J., Kim, D. H., Han, I. O., Lee, E. H., Chung, S. K., Joo, C. K., "*Hydrogen Peroxide is a Novel Inducer of Connective Tissue Growth Factor,*" BIOCHEM. BIOPHYS. RES. COMMUN. 284(4):966-971 (2001).

Schwab, J. M., Postler, E., Nguyen, T. D., Mittelbronn, M., Meyermann, R., Schluesener, H. J., "*Connective Tissue Growth Factor is Expressed by a Subset of Reactive Astrocytes in Human Cerebral Infarction,*" NEUROPATHOL. APPL. NEUROBIOL. 26(5):434-440 (2000).

Schwab, J. M., Beschorner, R., Nguyen, T. D., Meyermann, R., Schluesener, H. J., "*Differential Cellular Accumulation of Connective Tissue Growth Factor Defines a Subset of Reactive Astrocytes, Invading Fibroblasts, and Endothelial Cells Following Central Nervous System Injury in Rats and Humans,*" J. NEUROTRAUMA 18(4):377-388 (2001).

Shepard et al., *IOVS* 42:3173 (2001).

Wang et al., *Mol. Vis.* 7:89-94 (2001).

Willson, T. M. et al., "*The PPARs: from orphan receptors to drug discovery*" J MED CHEM 43(4):527-550 (2000).

Woodgett, J. R., "*Judging a protein by more than its name: GSK-3*" SCI STKE 2001(100):RE12 (2001).

Zaharevitz, D. W. et al., "*Discovery and initial characterization of the paullones, a novel class of small-molecule inhibitors of cyclin-dependent kinases*" CANCER RES 59(11):2566-2569 (1999).

We claim:

1. A method for lowering intraocular pressure and providing neuroprotection to a patient in need thereof, said method comprising administering a therapeutically effective amount of a composition comprising at least one non-nucleotide or non-protein agent that inhibits expression, signaling or biological functions of connective tissue growth factor (CTGF), and a pharmaceutically acceptable carrier, and wherein said agent is GW-8510, purvalanol A, roscovitine, or a combination thereof.

2. The method of claim 1, wherein said administering is by topical application, intracamerally or via an implant.

3. The method of claim 1, wherein the total concentration of said CTGF inhibitor in said composition is from 0.01% to 2%.

4. The method of claim 1, wherein said patient suffers from glaucoma or ocular hypertension.

5. The method of claim 4, wherein said glaucoma is normal-tension glaucoma.

6. A method for lowering intraocular pressure in a patient in need thereof, said method comprising administering a therapeutically effective amount of a composition comprising at least one non-nucleotide or non-protein agent that inhibits expression, signaling, or biological functions of connective tissue growth factor (CTGF), and a pharmaceutically acceptable carrier, and wherein said agent is GW-8510, purvalanol A, roscovitine, or a combination thereof.

7. The method of claim 6, wherein said administering is by topical application, intracamerally or via an implant.

8. The method of claim 6, wherein the total concentration of said CTGF inhibitor in said composition is from 0.01% to 2%.

9. The method of claim 6, wherein said patient suffers from glaucoma or ocular hypertension.

10. The, method of claim 9, wherein said glaucoma is normal-tension glaucoma.

11. A method for preventing the visual field loss associated with Primary Open Angle Glaucoma (POAG), said method comprising administering to a patient in need thereof a composition comprising a non-nucleotide or non-protein agent that modulates the expression of Connective Tissue Growth Factor (CTGF) such that intraocular pressure is controlled and protection is provided to retinal ganglion cells or to the optic nerve head, and wherein said agent is GW-8510, purvalanol A, roscovitine, or a combination thereof.

* * * * *